United States Patent [19]

Hester, Jr.

[11] 4,012,413
[45] * Mar. 15, 1977

[54] ORGANIC COMPOUNDS AND PROCESS

[75] Inventor: Jackson B. Hester, Jr., Galesburg, Mich.

[73] Assignee: The Upjohn Company, Kalamazoo, Mich.

[ * ] Notice: The portion of the term of this patent subsequent to Oct. 23, 1990, has been disclaimed.

[22] Filed: Feb. 14, 1975

[21] Appl. No.: 550,120

Related U.S. Application Data

[63] Continuation of Ser. No. 361,348, May 17, 1973, abandoned, which is a continuation-in-part of Ser. No. 138,827, April 28, 1971, Pat. No. 3,759,943.

[52] U.S. Cl. .................. 260/308 R; 260/247.5 EP; 260/268 R; 260/293.59; 424/248.52; 424/250; 424/248.58; 424/267; 424/269; 424/248.4

[51] Int. Cl.$^2$ ........................................ C07D 487/04
[58] Field of Search .............................. 260/308 R

[56] References Cited

UNITED STATES PATENTS 3,391,138 7/1968 Archer et al. ............... 260/239 BD
3,767,661 10/1973 Hester ........................... 260/308 R

OTHER PUBLICATIONS

Allgeier et al., Chem. Abstracts, vol. 77, Abstract No. 126711r, (1972).

Primary Examiner—Raymond V. Rush
Attorney, Agent, or Firm—Hans L. Berneis

[57] ABSTRACT

Compounds of the formula:

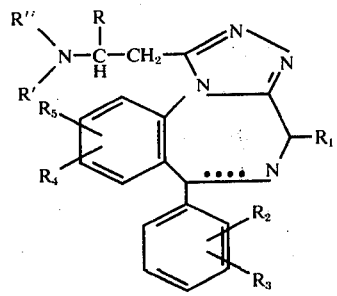

X wherein R is hydrogen, methyl, or ethyl; wherein R' and R" are hydrogen, alkyl of 1 to 3 carbon atoms, inclusive, wherein $R_1$ is hydrogen or methyl defined as above; wherein $R_2$, $R_3$, $R_4$, and $R_5$ are selected from the group consisting of hydrogen, alkyl defined as above, halogen, nitro, trifluoromethyl, and alkoxy and alkylthio, in which the carbon chain moieties are of 1 to 3 carbon atoms, inclusive; and wherein the 5 to 6 nitrogen-carbon linkage is selected from the group consisting of double bonds and single bonds, are produced by a variety of multistep processes.

The new compounds of formula X above and the pharmacologically acceptable acid addition salts thereof have oral and parenteral sedative and tranquilizing activity, and anti-depressant activity and can be employed for tranquilizing mammals as well as combating anxiety and depressions.

4 Claims, No Drawings

ORGANIC COMPOUNDS AND PROCESS

CROSS REFERENCE TO RELATED APPLICATION

This application is a continuation of application Ser. No. 361,348, filed May 17, 1973 and now abandoned, which is a continuation-in-part of application Ser. No. 138,287, filed April 28, 1971, now U.S. Pat. 3,789,943.

BACKGROUND OF THE INVENTION

Field of the Invention

This invention is directed to novel organic compounds and is more specifically concerned with aminotriazolobenzodiazepines of the formulae below and methods of production thereof.

The novel compounds and the processes therefor can be illustratively represented as follows:

Scheme A

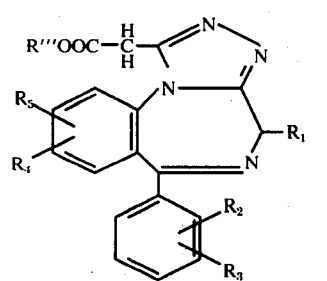

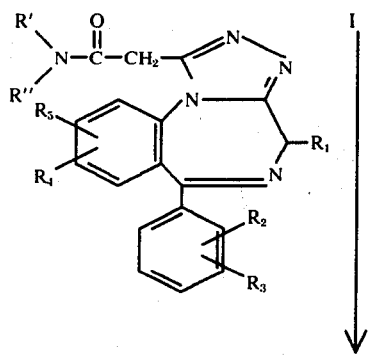

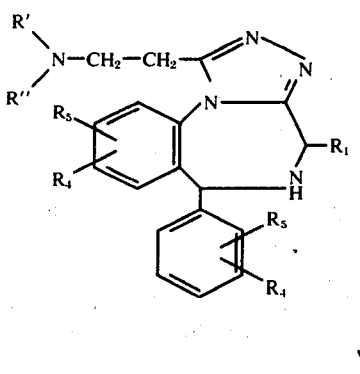

Scheme A -continued

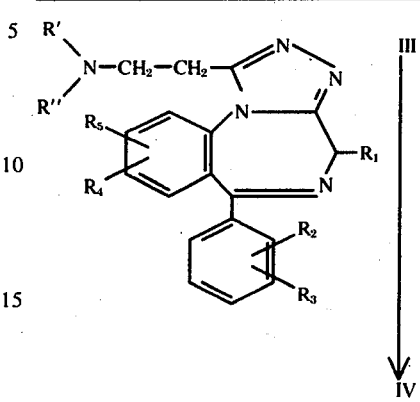

The products in which R is hydrogen as well as methyl or ethyl are produced by a Scheme B process Scheme B

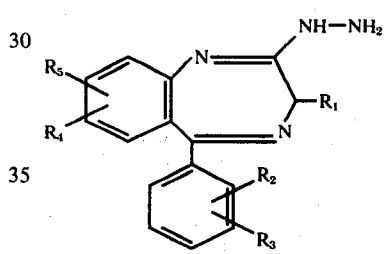

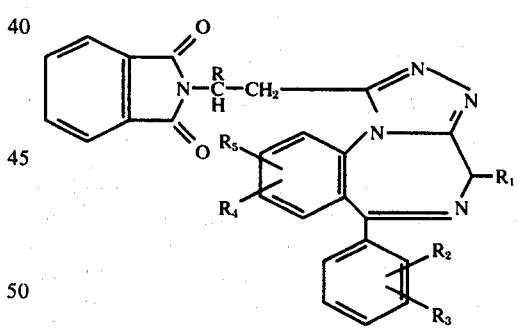

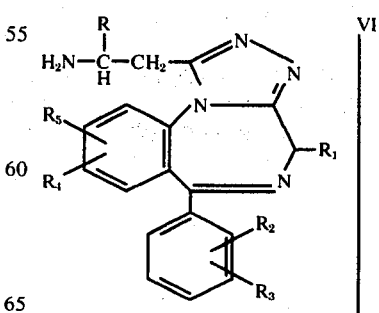

-continued
Scheme B

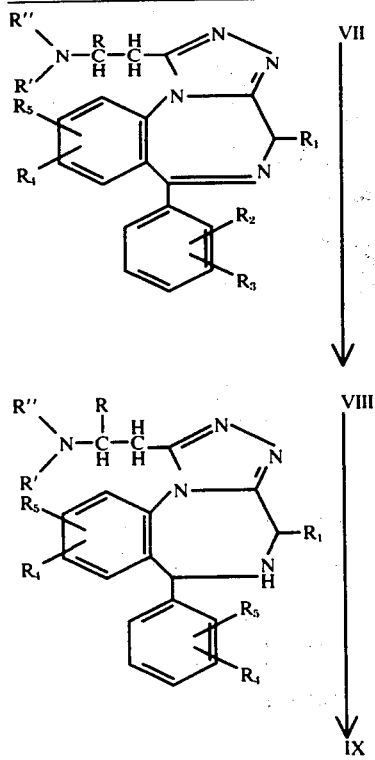

wherein R is hydrogen, methyl or ethyl; wherein R' and R'' are hydrogen, alkyl of 1 to 3 carbon atoms, inclusive; wherein R''' is alkyl defined as above, wherein $R_1$ is hydrogen or methyl defined as above; and wherein $R_2$, $R_3$, $R_4$, and $R_5$ are selected from the group consisting of hydrogen, alkyl defined as above, halogen, nitro, trifluoromethyl, and alkoxy and alkylthio, in which the carbon chain moiety is of 1 to 3 carbon atoms, inclusive.

The process of Method A of this invention comprises: treating an ester of formula I with ammonia or an amine at a temperature between 25°–200° C. in an organic solvent to obtain an amide of formula II; reducing the amide with borane ($B_2H_6$) or aluminum hydride ($AlH_3$) in an organic solvent between room temperature and the reflux temperature of the reaction mixture to obtain the amine III of the formula above and oxidizing III e.g. with an oxidizing agent selected from the group consisting of dichlorodicyanoquinone, manganese dioxide, ruthenium tetroxide or with diethylazodicarboxylate to obtain the benzodiazepine of formula IV.

The process of method B of this invention comprises: treating a hydrazino compound of formula V with a reactive derivative of a β-phthalimidocarboxylic acid (e.g. the acid chloride or bromide) of the formula:

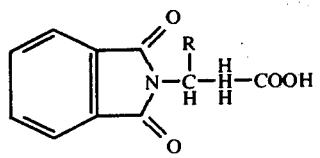

wherein R is defined as above, or with the free acid and a dehydrating agent e.g. carbonyldimidazole and warming the resulting product in a solvent such as acetic acid, to obtain the corresponding compound VI, treating VI with hydrazine to obtain VII and alkylating VII, if desired to obtain VIII. If R' and R'' are not identical this reaction must be carried out with one equivalent of aldehyde to one equivalent of compound VII and if desired with another acid aldehyde to obtain an amine VIII with two different alkyl groups. Compound VIII can be reduced with diborane to give the saturated compound IX.

The active compounds of this invention can be presented by the summary formula X:

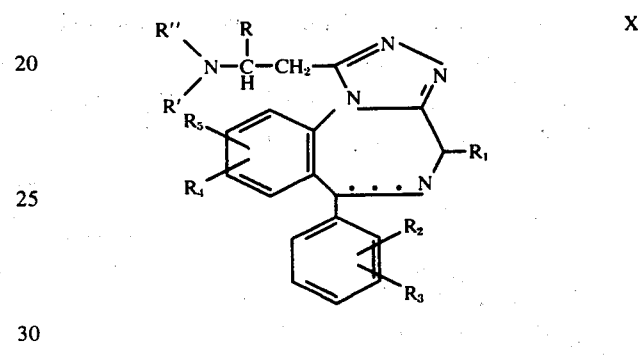

wherein R is hydrogen, methyl, or ethyl; wherein R' and R'' are hydrogen or alkyl of 1 to 3 carbon atoms, inclusive; wherein $R_1$ is hydrogen or methyl defined as above; wherein $R_2$, $R_3$, $R_4$, and $R_5$ are selected from the group consisting of hydrogen, alkyl defined as above, halogen, nitro, trifluoromethyl, and alkoxy and alkylthio, in which the carbon chain moiety is of 1 to 3 carbon atoms, inclusive, and in which the 5 to 6 nitrogen-carbon linkage is selected from the group consisting of double bonds and single bonds, and the pharmacologically acceptable acid addition salts thereof.

The more desirable products have the formula XI

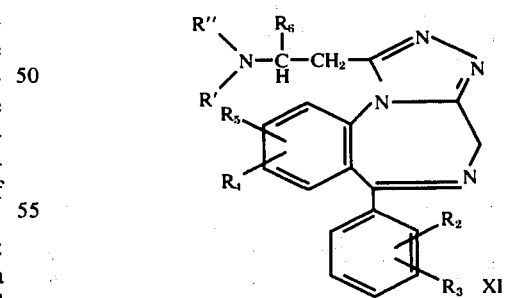

wherein $R_6$ is hydrogen or methyl; wherein R' and R'' are hydrogen or alkyl to 1 to 3 carbon atoms, inclusive; wherein $R_2$, $R_3$, $R_4$, and $R_5$ are selected from the group consisting of hydrogen, halogen, nitro, and trifluoromethyl, and the pharmacologically acceptable acid addition salts thereof.

Most preferred are the compounds of formula XII:

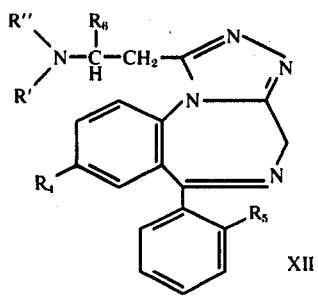

wherein $R_6$ is hydrogen or methyl; wherein $R'$ and $R''$ are hydrogen or alkyl of 1 to 3 carbon atoms, inclusive; wherein $R_2$ and $R_4$ are selected from the group consisting of hydrogen and chlorine, and the pharmacologically acceptable acid addition salts thereof.

DESCRIPTION OF THE PREFERRED EMBODIMENT

Lower alkyl groups of 1 to 3 carbon atoms, inclusive, are exemplified by methyl, ethyl, and propyl.

The carbon chain moiety of alkoxy and alkylthio which is of 1 to 3 carbon atoms, inclusive, is defined as loweralkyl of 1 to 3 carbon atoms, inclusive, as above.

The term halogen includes fluorine, chlorine, and bromine.

The novel compounds of the formula X (including the subgeneric species XI and XII) and pharmacologically acceptable acid addition salts thereof, have sedative, tranquilizing and muscle relaxant effects and antidepressant activity in mammals and birds.

The pharmacologically acceptable acid addition salts of compounds of formula X (including the preferred compounds XI and XII) contemplated in this invention, are the hydrochlorides, hydrobromides, hydriodides, sulfates, phosphates, cyclohexanesulfamates, methanesulfonates, and the like, prepared by reacting a compound of formula X, XI, or XII with an excess of the selected pharmacologically acceptable acid.

Sedative effects of 1-(2-aminoethyl)-8-chloro-6-phenyl-4H-s-triazolo[4,3-a][1,4-benzodiazepine are shown by the following tests in mice:

Chimney test: [Med. Exp. 4, 11 (1961)]:

The effective intraperitoneal dosage for 50% of mice ($ED_{50}$) is 40 mg./kg. The test determines the ability of mice to back up and out of a vertical glass cylinder within 30 seconds. At the effective dosage, 50% of the mice failed doing it.

Dish test:

Mice in Petri dishes (10 cm. diameter, 5 cm. high, partially embedded in wood shavings), climb out in a very short time, when not treated. Mice remaining in the dish for more than 3 minutes indicates tranquilization. $ED_{50}$ equals the dose of test compound at which 50% of the mice remain in the dish. The $ED_{50}$ (intraperitoneal administration) in this test was 80 mg./kg.

Pedestal test:

The untreated mouse leaves the pedestal in less than a minute to climb back to the floor of the standard mouse box. Tranquilized mice will stay on the pedestal for more than one minute. The $ED_{50}$ (intraperitoneal administration) is 100 mg./kg.

Nicotine antagonism test:

Mice in a group of 6 are injected with the test compound, 1-(2-aminoethyl)-8-chloro-6-phenyl-4H-s-triazolo[4,3-a][1,4]benzodiazepine. Thirty minutes later the mice including control (untreated) mice are injected with nicotine salicylate (2 mg./kg.). The control mice show overstimulation, i.e., (1) running convulsions followed by (2) tonic extensor-fits, followed by (3) death. An intraperitoneal dosage of 6.3 mg./kg. of the test compound protected 50% of the mice against (3).

The anti-depressant action:

The main function of an antidepressant is to return the depressed individual up to normal function. This should be carefully differentiated from psychic stimulants such as the amphetamines which produce overstimulation in the normal individual.

Many different methods have been and are used to evaluate anti-depressant activity. In general these methods involve antagonism of a depressant such as reserpine or tetrabenazine or a synergistic increase of the toxicity of certain compounds (i.e. yohimbine or 3,4-dihydroxyphenalanine) and comparison of the drug action of the new compound with other known antidepressants. No single test alone can determine whether or not a new compound is an antidepressant or not, but the profile evidenced by various tests will establish the anti-depressant action if present. A number of such tests are described below.

Hypothemic tests with oxotremorine: [1-[4-(pyrrolidinyl)-2-butynyl]-2-pyrrolidinone].

Oxotremorine (as well as apomorphine and tetrabenazine) produces hypothermic responses in mice. This response is blocked by anticholinergics and antidepressants such as atropine and imipramine.

Oxotremorine produces a very pronounced hypothermia which reaches a peak 60 minutes after administration.

At 0.6 mg./kg. the body temperature of a mouse is decreased about 13° F. (when the mouse is kept at room temperature). This temperature decrease is antagonized by anti-depressants e.g. desipramine, imipramine, doxepine, and others as can be seen from Table I.

TABLE I

| Compound | Dose mg./kg., I. P. | Absorption Time (min) | Body Temperature ° F-Change From Vehicle Control After Minutes | | | |
|---|---|---|---|---|---|---|
| | | | 15 | 30 | 60 | 90 |
| oxotremorine (Control) | 0.6 | | −5.8 | −11.6 | −13.2 | −8.0 |
| Desipramine | 25 | 30 | −3.5 | −3.5 | −4.1 | −3.6 |

TABLE I-continued

Effect of Various Compounds on Oxotremorine-Induced Hypothermia in Mice

| Compound | Dose mg./kg., I.P. | Absorption Time (min) | Body Temperature °F-Change From Vehicle Control After Minutes | | | |
|---|---|---|---|---|---|---|
| | | | 15 | 30 | 60 | 90 |
| Imipramine | 25 | 30 | −0.4 | −3.3 | −5.6 | −6.4 |
| Iprindole | 25 | 30 | −6.3 | −11.8 | −12.8 | −11.9 |
| Doxepine | 25 | 30 | −2.3 | −7.1 | −11.0 | −12.3 |
| Amitriptyline | 25 | 30 | +0.7 | −2.4 | −5.4 | −6.8 |
| Amphetamine | 5 | 30 | −1.5 | −4.3 | −4.4 | −2.2 |

The present compound was treated as follows:

Four male mice of 18–22 g. (Strain CF=Carworth Farms) were injected intraperitoneally with 1 mg. of oxotremorine. The lowering of the body temperature was measured rectally with an electronic thermometer, before and 30 minutes after drug administration. After the drug administration the mice were kept at 19° C. in cages. A raise of 4 degrees Fahrenheit over the oxotremorine body temperature was taken as indicative of anti-depressant activity. A dosage of 4.4 mg./kg. of the test compound produced the desired result.

Potentiation of yohimbine aggregation toxicity: the $LD_{50}$ of yohimbine hydrochloride [YCl] in mice is 45 mg./kg. i.p. Administration of 30 mg./kg. of [YCl] was non-lethal. If an anti-depressant is administered prior to the [YCl] (30 mg./kg.), the lethality of the [YCl] is increased.

As a control ten male CF mice, 18–22 g., are injected with [YCl] (30 mg./kg.) in saline solution. Groups of ten mice are injected with varying doses of the antidepressant 30 minutes before the administration of [YCl] (30 mg./kg.). After 2 hours the $LD_{50}$'s are determined. No mice or only one mouse is killed from 30 mg./kg. of [YCl]. In the presence of an anti-depressant an increase in the toxicity of [YCl] is found. The $ED_{50}$ value of the test compound in causing 50% of the mice to die is 50 mg./kg.

Potentiation of apomorphine gnawing: a group of 4 mice (male, CF, 18–22 g. ) are administered the test compound intraperitoneally one hour prior to the subcutaneous injection of apomorphine hydrochloride 1 mg./kg. The mice are then placed in a plastic box (6 × 11 × 5) lined at the bottom with a cellophane-backed, absorbent paper. The degree of damage to the paper at the end of 30 minutes is scored from zero to 4. The scores 3 and 4 indicated that the compound is a potentiator of apomorphine in this test. The test compound gave positive test at 35 mg./kg.

In the same testing system, 1-[2-dimethylamino)ethyl]-8-chloro-6-phenyl-4H-s-triazolo[4,3-a]benzodiazepine bis (cyclohexanesulfamate (A) and 1-[2-aminopropyl]-8-chloro-6-phenyl4H-s-triazolo[4,3-a][1,4]benzodiazepine bis tosylate (B) showed;

| | A | B |
|---|---|---|
| Chimney test | 45 | 100 |
| Dish | 36 | >100 |
| Pedestal | >50 | >100 |
| Nicotine (3) | 4.5 | 32 |
| Oxotremorine | 12.5 | 4.4 |
| Yohimbine | >50 | 21 |
| Apomorphine | >50 | 25 |

This indicates that compounds (A) and (B) are essentially anti-depressant with low sedative activity.

The pharmaceutical forms of compound X including the preferred compounds XI and XII comtemplated by this invention include pharmaceutical compositions suited for oral, parenteral, and rectal use, e.g., tablets, powder packets, cachets, dragees, capsules, solutions, suspensions, sterile injectable forms, suppositories, bougies, and the like. Suitable diluents or carries such as carbohydrates (lactose), proteins, lipids, calcium phosphate, cornstarch, stearic acid, methylcellulose and the like may be used as carriers or for coating purposes. Water and oils, e.g. coconut oil, sesame oil, safflower oil, cottonseed oil, peanut oil may be used for preparing solutions or suspensions of the active drug. Sweetening, coloring and flavoring agents may be added.

For mammals and birds food premixes, with starch, oatmeal, dried fishmeat, fishmeal, flour, and the like can be prepared.

As anti-depressants and tranquilizers the compounds of formula X and their salts can be used in dosages of 1–50 mg./kg. preferably 5–20 mg./kg. in oral or injectable preparations as described above, to alleviate tension and anxiety in mammals, or birds, such as e.g., occurs when animals are shipped. Larger mammals of more than 10 kg. body weight are tranquilized at the low dosages, whereas the small test animals need the higher dosages per kilogram.

Other acid addition salts of the compounds of formula X can be made, such as the fluosilicic acid addition salts which are useful mothproofing compounds or the trichloroacetates useful as herbicides against Johnson grass, Bermuda grass, yellow foxtail, and green foxtail, and quack grass.

The starting materials of formula I (Scheme A) of this invention, substituted or unsubstituted 6-phenyl-4H-s-triazolo[4,3-a][1,4]benzodiazepine-1-acetic acid esters are produced from 6-phenyl-4H-s-triazolo[4,3-a][1,4]benzodiazepine-1-acetonitriles as shown in U.S. Pat. No. 3,701,782 and in Preparation 2. The acetonitriles are produced as in preparation 1 from 1,3-dihydro-5-phenyl-2H-1,4-benzodiazepine-2-thiones [these thiones, described by G. A. Archer et al., J. Org. Chem.

29, 231 (1964), were made from the corresponding 1,3-dihydro-5-phenyl-2H-1,4-benzodiazepin-2-ones, Sternbach et al., J. Org. Chem. 27, 3788 (1962)].

In carrying out the process of this invention according to Scheme A a compound of formula I is reacted with aqueous ammonia or an aqueous lower dialkylamine in dimethylformamide, dioxane, tetrahydrofuran, a lower alkanol, or the like. This reaction is also carried out under anhydrous conditions using a polyhydroxy compound, e.g. ethylene glycol, diethyleneglycol, glycerol and the like as a cosolvent to catalyse the reaction. Also an N-heterocyclicamine can be condensed with compounds of formula I, preferably in a solvent, e.g. dimethylformamide, dimethylacetamide, a lower alkanol, ethylene glycol, or the like, between 25°–200° C. to give the corresponding N-heterocyclicamide. The N-heterocyclicamines useful for this purpose are piperidine, pyrrolidine, morpholine, hexamethyleneimine and 4-methyl- or 4-phenylpiperazine.

The product (II) obtained is recovered and purified by standard methods e.g. extraction, chromatography, and crystallization.

Compound II, in ether or tetrahydrofuran when treated with diborane ($B_2H_6$) or aluminum hydride between 25°–80° C. yields the amine of formula III which is recovered and purified by conventional means e.g. extraction, chromatography, and recrystallization.

Compound III can be oxidized in part with active manganese dioxide preferably in benzene, tetrahydrofuran or other anhydrous solvent or with ruthenium tetroxide in a solvent such as chloroform or carbontetrachloride, to give compound IV.

Instead of manganese dioxide or ruthenium tetroxide diethyl azodicarboxylate is useful, or, as preferred, dichlorodicyanoquinoline. The temperature for this reaction is between 25°–80° C. and the time is between 1 and 18 hours. The product IV is isolated and purified by conventional means e.g. extraction, chromatography, and recrystallization.

In carrying out the process of this invention according to Scheme B, the starting compounds used are of formula V [(Meguro, Tetrahedron Letters, 4039 (1970); Dutch patent application No. 69 16543; or made from a 1,3-dihydro-5-phenyl-2H-1,4-benzodiazepine-2-thione by treatment with hydrazine as disclosed in Preparation 12].

To obtain the compound of formula VI a selected β-phthalimidocarboxylic acid [Chem. Ber. 38,633 (1905); J. Am. Chem. Soc. 76, 5651 (1954)] is admixed in situ in an organic solvent such as tetrahydrofuran, dioxane, or ether with a compound such as carbonyldiimidazole at 0° to 25° C. This mixture is allowed to stand for 1 to 2 hours, and the selected compound of formula V is then added to the mixture and the reaction is allowed to proceed between 0° to 30° C. for 1 to 18 hours. Thereafter the resulting product is recovered e.g. by filtering or evaporating the solvent, and the crude material is heated between 100 to 120 for 30–60 minutes in a suitable organic solvent e.g. acetic acid to give the corresponding compound of formula VI above, which can be isolated and purified by standard procedures such as extraction, chromatography and recrystallization.

Compounds of formula VI are converted into compounds of formula VII by heating with hydrazine or hydrazine hydrate. In the preferred embodiment of this invention, the reaction is carried out at 50°–78° C. during 1 to 5 hours in solvents such as methanol, or preferably ethanol. The product can be isolated and purified by conventional procedures such as extraction, chromatography, and crystallization.

Alkylation of compound VII can be obtained by treating VII with an aldehyde of the formula $R_7CHO$ in the presence of sodium cyanoborohydride ($NaBH_3CN$) wherein $R_7$ is hydrogen, methyl or ethyl to give a compound of formula VIII.

In the preferred embodiment of this reaction compound VII in solution or suspension e.g. in acetonitrile, an aldehyde ($R_7CHO$) as defined above, and an organic acid e.g. acetic or propionic acid are cooled to 0°–5° C. and then treated with sodium cyanoborohydride. The mixture is allowed to stand at low temperatures, 0° to 5° C., for 15–60 minutes, and then allowed to warm up to room temperature (20°–30° C.) and stand for 1–4 hours. During the reaction the pH is adjusted to about 7 by periodically adding additional acid. The product VIII thus obtained is isolated and purified by conventional methods, such as concentration, extraction, chromatography, and crystallization.

When 2 or more equivalents of acid aldehydes is used per equivalent of compound VII, a compound VIII in which $R'=R''$ is obtained. When one equivalent of acid aldehyde is used per equivalent of compound VII, a compound VIII is obtained in which $R'=$alkyl and $R''$ is hydrogen. Such a compound can be treated again with an acid aldehyde to give a product VIII in which each $R'$ and $R''$ are alkyl, and can be different alkyl groups.

The Compound VIII can be converted to compound IX by reduction with borane or aluminum hydride under conditions as shown for the prior-described step II → III. Product IX is recovered as mentioned above for product III.

The following Preparations and examples are illustrative of the processes and products of the present invention, but are not to be construed as limiting.

Preparation 1

8-Chloro-6-phenyl-4H-s-triazolo[4,3-a][1,4]-benzodiazepine-1-acetonitrile

A mixture of 1,3-dihydro-7-chloro-5-phenyl-2H-1,4-benzodiazepine-2-thione (5.72 g., 0.02 mole), cyanoacetic acid hydrazide (5.95 g., 0.06 mole) and n-butylalcohol (275 ml.) is refluxed for 7.5 hours with a slow stream of nitrogen bubbling through the mixture. The mixture is then concentrated in vacuo. The resulting residue is suspended in water and extracted with methylene chloride. The extract was dried and concentrated. The residue is chromatographed on silica gel (400 g.) with 2% methanol-98% $CHCl_3$. The product eluted from the column is crystallized from ethyl acetate-Skellysolve B hexanes to give 2.62 g. of 8-chloro-6-phenyl-4H-s-triazolo[4,3a][1,4]benzodiazepine-1-acetonitrile of melting point 198°–201° C.

Anal. calcd. for $C_{18}H_{12}ClN_5$: C, 64.77; H, 3.63; Cl, 10.62. Found: C, 64.52; H, 3.86; Cl, 10.51.

Preparation 2

8-Chloro-6-phenyl-4H-s-triazolo[4,3-a][1,4]-benzodiazepine-1-acetic acid methyl ester A stirred mixture of 8-chloro-6-phenyl-4H-s-triazolo[4,3-a][1,4]benzodiazepine-1-acetonitrile (1.00 g., 0.003 mole) methanol (2 ml.) and ether (6 ml.) is cooled in a salt-ice bath saturated with a stream of anhydrous hydrogen chloride during 15 minutes. The mixture is allowed to warm slowly to ambient temperature and stand for 18 hours; it is then poured into water. This mixture is neutralized with sodium bicarbonate and extracted with chloroform. The extract is washed with brine, dried over anhydrous magnesium sulfate and then concentrated. The residue is crystallized from methanol to give 0.149 g. of a by-product of melting point 184.5°–188° C. (d.). The mother liquor is crystallized from methanol-ethyl acetate to give 0.126 g. of a by-product of melting point 205.5°–207.5° C. (d.). The mother liquor from this crystallization is concentrated and chromatographed on silica gel (50 g.) with 2% methanol-98% chloroform. The first compound eluted from the column is crystallized from methanol-ethyl acetate to give 8-chloro-6-phenyl-4H-s-triazolo[4,3-a][1,4]benzodiazepine-1-acetic acid methyl ester in two crops: 0.169 g. of melting point 202°–203.5° C. (d.) and 0.125 g. of melting point 200.5°–202.5° C. (d.). The analytical sample had a melting point of 202°–203° C.

Anal. calcd. for $C_{19}H_{15}ClN_4O_2$: C, 62.21; H, 4.12; Cl, 9.67; N, 15.28. Found: C, 62.32; H, 4.14; Cl, 10.15; N, 15.33.

Preparation 3

N,N-dimethyl-8-chloro-6-phenyl-4H-s-triazolo[4,3-a][1,4]benzodiazepine-1-acetamide A suspension of 8-chloro-6-phenyl-4H-s-triazolo[4,3-a]-[1,4]benzodiazepine-1-acetic acid methyl ester (0.367 g., 0.001 mole) in 25% aqueous dimethylamine (5 ml.) and dimethylamine hydrochloride (81.5 mg.) and stirred under nitrogen at ambient (23°–25° C.) temperature for 18 hours. It is poured into cold water, saturated with sodium chloride and extracted with methylene dichloride. The extract is washed with a dilute sodium chloride solution, dried over anhydrous potassium carbonate and concentrated in vacuo. The resulting residue is treated successively with xylene and toluene with concentration after each addition. The resulting material is crystallized from methanol-ethyl acetate to give 0.173 g. of N,N-dimethyl-8-chloro-6-phenyl-4H-s-triazolo[4,3-a][1,4]benzodiazepine-1-acetamide of melting point 204°–205.5° C.

Anal. calcd. for $C_{20}H_{18}ClN_4$: C, 63.24; H, 4.78; Cl, 9.35; N, 1844. Found: C, 63.01; H, 4.83; Cl, 9.39; N, 1841.

Preparation 4

N,N-Dimethyl-8-chloro-6-(o-chlorophenyl)-4H-s-triazolo[4,3-a][1,4]benzodiazepine-1-acetamide In the manner given in Preparation 3, 8-chloro-6-(o-chlorophenyl)-4H-s-triazolo[4,3-a][1,4]benzodiazepine-1-acetic acid methyl ester is reacted with dimethylamine in dimethylformamide to give N,N-dimethyl-8-chloro-6-(o-chlorophenyl)-4H-s-triazolo[4,3-a][1,4]benzodiazepine-1-acetamide.

Preparation 5

N,N-dimethyl-6-(o-chlorophenyl)-4H-s-triazolo[4,3-a][1,4]benzodiazepine-1-acetamide In the manner given in Preparation 3, 6-(o-dichlorophenyl)-4H-s-triazolo[4,3-a][1,4]benzodiazepine-1-acetic acid methyl ester is reacted with dimethylamine in dimethyl formamide to give N,N-dimethyl-6-(o-chlorophenyl)-4H-s-triazolo[4,3-a][1,4]benzodiazepine-1-acetamide.

Preparation 6

N,N-Dimethyl-8-chloro-6-(2,6-difluorophenyl)-4H-s-triazolo[4,3-a][1,4]benzodiazepine-acetamide In the manner given in Preparation 3, 8-chloro-6-(2,6-difluorophenyl)-4H-s-triazolo[4,3-a][1,4]benzodiazepine-1-acetic acid methyl ester is reacted with dimethylamine in dimethylformamide to give N,N-dimethyl-8-chloro-6-(2,6-difluorophenyl)-4H-s-tiazolo[4,3-a][1,4]benzodiazepine-1-acetamide.

Preparation 7

N,N-Tetramethylene-4-methyl-8-nitro-6-(m-bromophenyl)-4H-s-triazolo[4,3-a][1,4]benzodiazepine-1-acetamide In the manner given in Preparation 3, 4-methyl-8-nitro-6-(m-bromophenyl)-4H-s-triazolo[4,3-a][1,4]benzodiazepine-1-acetic acid ethyl ester is reacted with pyrrolidine in dimethylformamide to give N,N-tetramethylene-4-methyl-8-nitro-6-(m-bromophenyl)-4H-s-triazolo[4,3-a][1,4]-benzodiazepine-1-acetic acid ethyl ester is reacted with hexamethyleneimine in dimethylformamide to give N,N-hexamethylene-10-methoxy-6-[p-(methylthio)phenyl]-4H-s-triazolo[4,3-a][1,4]benzodiazepine-1-acetamide.

Preparation 10

N-Methyl-7-bromo-8-trifluoromethyl-6-(m-nitrophenyl)-4H-s-triazolo[4,3-a][1,4]benzodiazepine-1-acetamide In the manner given in Preparation 3, 7-bromo-8-trifluoromethyl-6-(m-nitrophenyl)-4H-s-triazolo[4,3-a][1,4]-benzodiazepine-1-acetic acid methyl ester is reacted with methylamine in diemethylformamide to give N-methyl-7-bromo-8-trifluoromethyl-6-(m-nitrophenyl)-4H-s-triazolo[4,3-a]-[1,4]benzodiazepine-1-acetamide.

Preparation 11

N-Methyl-N-ethyl-4-methyl-8-fluoro-6-(o-fluorophenyl)-4H-s-triazolo[4,3-a][1,4]benzodiazepine-1-acetamide In the manner given in Preparation 3, 4-methyl-8-fluoro-6-(o-fluorophenyl)-4H-s-triazolo[4,3-a][1,4-benzodiazepine-1-acetic acid methyl ester is reacted with methylethylamine in dimethylformamide to give N-methyl-N-ethyl-4-methyl-8-fluoro-6-(o-fluorophenyl)-4H-s-triazolo[4,3-a]-[1,4]benzodiazepine-1-acetamide.

Preparation 12

7-Chloro-2-hydrazino-5-phenyl-3H-1,4-benzodiazepine

A mixture of 7-chloro-1,3-dihydro-5-phenyl-2H-1,4-benzodiazepine-2-thione and hydrazine hydrate is allowed to stand for 72 hours at about 25° C. After evaporation of the ethanol, the solid products obtained are recrystallized from methylene chloride-benzene to give 7-chloro-2-hydrazino-5-phenyl-3H-1,4-benzodiazepine of melting point 204°–207° C.

EXAMPLE 1

1-[2-(Dimethylaino)ethyl]-8-chloro-5,6-dihydro-6-phenyl-4H-s-triazolo[4,3-a][1,4]benzodiazepine To a suspension of 9.12 g. (0.024 mole) of N,N-dimethyl-8-chloro-6-phenyl-4H-s-triazolo[4,3-a][1,4]benzodiazepine-1-acetamide in 200 ml. of tetrahydrofuran, cooled in an ice bath, is slowly added in a nitrogen atmosphere 100 ml. of a 1 M solution of borane in tetrahydrofuran. The reaction mixture is kept in the ice-bath for 35 minutes, at ambient temperature (22°–25° C.) for 14 hours and then heated to reflux and kept at reflux for 1 hour and 10 minutes.

The reaction mixture is cooled and treated slowly with 15 ml. of 6N hydrochloric acid. This mixture is boiled for 2 hours 35 minutes with distillation. During this period methanol (130 ml.) is added slowly so that the volume of the reaction mixture remains about constant. The resulting mixture is concentrated in vacuo and the residue is mixed with cold water neutralized with sodium bicarbonate and extracted with chloroform. The extract is washed with brine, dried over anhydrous sodium sulfate and concentrated in vacuo. This residue is dissolved in methanol (170 m/.), treated with a 25% aqueous solution of ethylenediamine (100 ml.) and refluxed for 2 hours 50 minutes. The resulting mixture is concentrated and the residue is mixed with water and extracted with chloroform. The extract is washed with brine, dried over anhydrous sodium sulfate and concentrated. The residue is chromatographed in silica gel (500 g.) with methanol. The product thus obtained is crystallized from ethyl acetate-Skellysolve B hexanes to give 1-[2-(dimethylamino)ethyl]-8-chloro-5,6-dihydro-6-phenyl-4H-s-triazolo-[4,3-a][1,4-benzodiazepine in three crops; 1.13 g. of melting point 131.5°–137° C., 0.684 g. of melting point 131.5°–138° C., and 0.167 g. of melting point 131.5°–138° C. The analytical sample had a melting point of 131°–137° C.

Anal. Calcd. for $C_{20}H_{22}ClN_5$: C, 65.30; H, 6.03; Cl, 9.63; N, 19.04. Found: C, 64.94; H, 6.07; Cl, 9.60; N, 18.78.

EXAMPLE 2

1-[2-(Dimethylamino)ethyl]-8-chloro-5,6-dihydro-6-(o-chlorophenyl)-4H-s-triazolo[4,3-a][1,4-benzodiazepine In the manner given in Example 1, N,N-dimethyl-8-chloro-6-(o-chlorophenyl)-4H-s-triazolo[4,3-a][1,4benzodiazepine-1-acetamide is reduced with borane to give 1-[2-(dimethylamino)ethyl]-8-chloro-5,6-dihydro-6-(o-chlorophenyl)-4H-s-triazolo[4,3-a][1,4-benzodiazepine.

EXAMPLE 3

1-[2-(Dimethylamino)ethyl]-5,6-dihydro-6-(o-chlorophenyl)-4H-s-triazolo[4,3-a][1,4]benzodiazepine In the manner given in Example 1, N,N-dimethyl-6-(o-chlorophenyl)-4H-s-triazolo[4,3-a][1,4]benzodiazepine-1-acetamide is reduced with borane to give 1-[2-(dimethylamino)ethyl]-5,6-dihydro-6-(o-chlorophenyl)-4H-s-triazolo-[4,3-a][1,4]benzodiazepine.

EXAMPLE 4

1-[2-(Diethylamino)ethyl]-8-chloro-5,6-dihydro-6-(2,6-difluorophenyl)-4H-s-triazolo[4,3-a][1,4]benzodiazepine In the manner given in Example 1, N,N-diethyl-8-chloro-(2,6-difluorophenyl)-4H-s-triazolo[4,3-a][1,4]benzodiazepine-1-acetamide was reduced with borane to give 1-[2-(diethylamino)ethyl]-8-chloro-5,6-dihydro-6-(2,6-difluorophenyl)-4H-s-triazolo[4,3-a][1,4]benzodiazepine.

EXAMPLE 5

1-(2-Pyrrolidinoethyl)-4-methyl-8-nitro-5,6-dihydro-6-(m-bromophenyl)-4H-s-triazolo[4,3-a][1,4]benzodiazepine In the manner given in Example 1, N,N-tetramethylene-4-methyl-8-nitro-6-(m-bromophenyl)-4H-s-triazolo[4,3-a]-[1,4]benzodiazepine-1-acetamide is reduced with aluminum hydride (instead of borane) to give 1-[2-pyrrolidinoethyl]-4-methyl-8-nitro-5,6-dihydro-6-(m-bromophenyl)-4H-s-triazolo[4,3-a][1,4]benzodiazepine.

EXAMPLE 6

1-(2-Piperidinoethyl)-7-trifluoromethyl-5,6-dihydro-6-(o-chlorophenyl)-4H-s-triazolo[4,3-a][1,4]benzodiazepine In the manner given in Example 1, N,N-pentamethylene-7-trifluoromethyl-6-(o-chlorophenyl)-4H-s-triazolo[4,3-a]-[1,4]benzodiazepine-1-acetamide is reduced with borane to give 1-(2-piperidinoethyl)-7-trifluoromethyl-5,6-dihydro-6-(o-chlorophenyl)-4H-s-triazolo[4,3-a][1,4benzodiazepine.

EXAMPLE 7

1-[2-(4-methylpiperazino)ethyl]-10-methoxy-5,6-dihydro-6-[p-(methylthio)phenyl]-4H-s-triazolo[4,3-a][1,4]-benzodiazepine In the manner given in Example 1, 1-[[10-methoxy-6-[(p-(methylthio)phenyl]-4H-s-triazolo[4,3-a][1,4]benzodiazepin-1-yl]acetyl]-4-methylpiperzine is reduced with borane to give 1-[2-(4-pentylpiperazino)ethyl]-10-methoxy-5,6-dihydro-6-[p-(methylthio)phenyl]-4H-s-triazolo[4,3-a][1,4]-benzodiazepine.

EXAMPLE 8

1-[2-(methylamino)ethyl]-7-bromo-8-(trifluoromethyl)-5,6-dihydro-6-(m-nitrophenyl)-4H-s-triazolo[4,3-a][1,4]benzodiazepine In the manner given in Example 1, N,methyl-7-bromo-8-(trifluoromethyl)-6-(m-nitrophenyl)-4H-s-triazolo[4,3-a][1,4]benzodiazepine-1-acetamide is reduced with borane to give 1-[2-(methylamino)ethyl)-7-bromo-8-(trifluoromethyl)-5,6-dihydro-6-(m-nitrophenyl)-4H-s-triazolo[4,3-a][1,4]benzodiazepine.

EXAMPLE 9

1-[2-(diethylamino)ethyl]-4-methyl-8-fluoro-5,6-dihydro-6-(o-fluorophenyl)-4H-s-triazolo[4,3-a][1,4]benzodiazepine In the manner given in Example 1, N,N-diethyl-4-methyl-8-fluoro-6-(o-fluorophenyl)-4H-s-triazolo[4,3-a]-[1,4]benzodiazepine-1-acetamide is reduced with borane to give 1-[2-diethylamino)ethyl]-4-methyl-8-fluoro-5,6-dihydro-6-(o-fluorophenyl)-4H-s-triazolo]4,3-a][1,4]benzodiazepine.

EXAMPLE 10

1-[2-(Dimethylamino)ethyl]-8-chloro-6-phenyl-4H-s-triazolo[4,3-a][1,4]benzodiazepine A stirred suspension of 368 mg. (0.001 mole) of 1-[2-(dimethylamino)ethyl]-8-chloro-5,6-dihydro-6-phenyl-4H-s-triazolo[4,3-a][1,4]benzodiazepine and 250 mg. of dichlorodicyanoquinone in dry benzene (20 ml.) is heated at reflux for 3 hours. The mixture is then cooled, filtered, and evaporated in vacuo. The residue is suspended in water and extracted with chloroform and chromatographed over 20 g. of silica gel with methanol. The resulting product is converted to its cyclohexanesulfamic acid salt which is crystallized from ethyl acetate-ethanol to give 1-[2-(dimethylamino)ethyl]-8-chloro-6-phenyl-4H-s-triazolo[4,3-a]-[1,4]benzodiazepine bis-cyclohexanesulfamate of melting point 132°-139° C.

EXAMPLE 11

1-[2-(dimethylamino)ethyl]-8-chloro-6-(o-chlorophenyl)-4H-s-triazolo[4,3-a][1,4]benzodiazepine In the manner given in Example 10, a suspension of 1-[2-dimethylamino)ethyl]-8-chloro-5,6-dihydro-6-(o-chlorophenyl)-4H-s-striazolo[4,3-a][1,4]benzodiazepine is oxidized with dichlorodicyanoquinone to give 1-[2-(dimethylamino)-ethyl]-8-chloro-6-(o-chlorophenyl)-4H-s-triazolo[4,3-a]-[1,4]benzodiazepine.

EXAMPLE 12

1-[2-(Dimethylamino)ethyl]-6-(o-chlorophenyl)-4H-s-triazolo[4,3-a][1,4]benzodiazepine In the manner given in Example 10, a suspension of 1-[2-(dimethylamino)ethyl]-5,6-dihydro-6-(o-chlorophenyl)-4H-s-triazolo[4,3-a][1,4-benzodiazepine is oxidized with dichlorodicyanoquinone to give 1-[2-(dimethylamino)ethyl]-8-chloro-6-(o-chlorophenyl)-4H-s-triazolo[4,3-a][1,4]benzodiazepine.

EXAMPLE 13

1-[2-(diethylamino)ethyl]-8-chloro-6-(2,6-difluorophenyl)-4H-s-triazolo[4,3-a][1,4]benzodiazepine In the manner given in Example 10, a suspension of 1-[2-(diethylamino)ethyl]-8-chloro-5,6-dihydro-6-(2,6-difluorophenyl)-4H-s-triazolo[4,3-a][1,4]benzodiazepine is oxidized with dichlorodicyanoquinone to give 1-[2-(diethylamino)-ethyl]-8-chloro-6-(26-diflurophenyl)-4H-s-triazolo[4,3-a]-[1,4]benzodiazepine.

EXAMPLE 14

1-(2-Pyrrolodinoethyl)-4-methyl-8-nitro-6-(m-bromophenyl)-4H-s-triazolo[4,3-a][1,4]benzodiazepine in the manner given in Example 10, a suspension of 1-(2-pyrrolidinoethyl)-4-methyl-8-nitro-5,6dihydro-6-(m-bromophenyl)-4H-s-triazolo[4,3-a][1,4]benzodiazepine is oxidized with dichlorodicyanoquinone to give 1-(2-pyrrolidinoethyl)-4-methyl-8-nitro-6-(m-bromophenyl)4H-s-triazolo[4,3-a][1,4]benzodiazepine.

EXAMPLE 15

1-(2-Piperidinoethyl)-7-trifluoromethyl-6-(o-chlorophenyl)-4H-s-triazolo[4,3-a][1,4]benzodiazepine In the manner given in Example 10, a suspension of 1-(2-piperidinoethyl)-7-trifluoromethyl-5,6-dihydro-6-(o-chlorophenyl)-4H-s-triazolo[4,3-a][1,4]benzodiazepine is oxidized with dichlorodicyanoquinone to give 1-(2-piperidinoethyl)-7-trifluoromethyl-6-(o-chlorophenyl)-4H-s-triazolo[4,3-a][1,4]benzodiazepine.

EXAMPLE 16

1-[2-(4-methylpiperazino)ethyl]-10-methoxy-6-[p-(methylthio)phenyl]-4H-s-triazolo[4,3-a][1,4]benzodiazepine In the manner given in Example 10, a suspension of 1-[2-(4-methylpiperazino)ethyl]-10-methoxy-5,6-dihydro-6-[p-(methylthio)phenyl]-4H-s-triazolo[4,3-a][1,4]benzodiazepine was oxidized with dichlorodicyanoquinone to give 1-[2-(4-methylpiperazino)ethyl]-10-methoxy-6-[p-(methylthio)-phenyl]-4H-s-triazolo[4,3-a][1,4]benzodiazepine.

EXAMPLE 17

1-(2-Morpholinoethyl)-8-bromo-6-(p-methoxyphenyl)-4H-s-triazolo[4,3-a][1,4]benzodiazepine In the manner given in Example 10, a suspension of 1-(2-morpholinoethyl)-8-bromo-5,6-dihydro-6-(p-methoxy-phenyl)-4H-s-triazolo[4,3-a][1,4]benzodiazepine was oxidized with dichlorodicyanoquinone to give 1-(2-morpholinoethyl)-8-bromo-6-(p-methoxy-phenyl)-4H-s-triazolo[4,3-a][1,4]benzodiazepine.

EXAMPLE 18

1-[2-(4-phenylpiperazino)ethyl]-8-chloro-6-(m-nitrophenyl)-4H-s-triazolo[4,3-a][1,4]benzodiazepine In the manner given in Example 10, a suspension of 1-[2-(4-phenylpiperazino)ethyl]-8-chloro-5,6-dihydro-6-(m-nitrophenyl)-4H-s-triazolo[4,3-a][1,4-benzodiazepine was oxidized with dichlorodicyanoquinone to give 1-[2-(4-phenylpiperazino)ethyl-8-chloro-6-(m-nitrophenyl)-4H-s-tiazolo-[4,3-a][1,4]benzodiazepine.

EXAMPLE 19

1-[2-(methylamino)ethyl]-7-bromo-8-trifluoromethyl-6-(m-nitrophenyl)-4H-s-triazolo[4,3[]1,4]benzodiazepine In the manner given in Example 10, a suspension of 1-[2-(methylamino)ethyl]-7-bromo-8-trifluoromethyl-5,6-dihydro-6-(m-nitrophenyl)-4H-s-triazolo[4,3-a][1,4]benzodiazepin is oxidized with dichlorodicyanoquinone to give 1-[2-(methylamino)ethyl]-7-bromo-8-trifluoromethyl-6-(m-nitrophenyl)-4H-s-triazolo[4,3-a][1,4]benzodiazepine.

EXAMPLE 20

N-[2-(8-chloro-6-phenyl]-4H-s-triazolo[4,3-a]-[1,4]benzodiazepin-1yl)ethyl]phthalimide and its ethyl acetate solvate 3-Phthalimidopropionic acid is prepared by heating β-alanine with phthalic anhydride [A. Schoberl and H. Braun, Ann. 542, 274 (1939)]. A stirred mixture of this acid (2.41 g., 0.011 mole) in tetrahydrofuran (20 ml.) is cooled in an ice bath and treated with carbonyldiimidazole (1.78 g., 0.011 mole). The mixture is kept at ambient temperature for 18 hours. The solid is collected by filtration, washed with tetrahydrofuran and dried to give 4.40 g. of crude 3-phthalimidopropionic acid, 2-(7-chloro-5-phenyl-3H-1,4-benzodiazepin-2-yl)hydrazide of melting point 145.5°–170° C. Additional product (0.224 g., of melting point 209°–216° dec.) is obtained by working up the filtrate.

A stirred mixture of this material (2 g.) and acetic acid (20 ml. is warmed, under nitrogen, in an oil bath maintained at 117° for 42 minutes. The solution is concentrated in vacuo and the residue is mixed with water and chloroform, neutralized with sodium bicarbonate and extracted with chloroform. The extract is washed with brine, dried over anhydrous sodium sulfate and concentrated. The residue is crystallized from methylene chloride-methanol-ethyl acetate (decolorizing with activated charcoal) to give 1.93 of N-[2-(8-chloro-6-phenyl-4H-s-triazolo[4,3-a][1,4]benzodiazepin-1-yl)ethyl]phthalimide as an ethyl acetate solvate which melts at 133°–134° with foaming, resolidifies and then melts at 225° C. The analytical sample is crystallized from methylene chloride-ethyl acetate and has a melting point of 130°–133.5° C. (foaming), melting point 224°–226° C.

Anal. calcd. for $C_{26}H_{18}ClN_5O_2 \cdot C_4H_8O_2$: C, 64.81; H, 4.71; Cl, 6.38; N, 12.59; EtOAc, 15.84. Found: C, 64.39; H, 4.81; Cl, 6.31; N, 12.49; EtOAc, 18.40.

The unsolvated product can be obtained by warming this material at 140°–150° in vacuo.

EXAMPLE 21

1-(2-Aminoethyl)-8-chloro-6-phenyl-4H-s-triazolo-[4,3-a][1,4]benzodiazepine

A stirred mixture of N-[2-(8-chloro-6-phenyl-4H-s-triazolo[4,3-a][1,4]benzodiazepin-1-yl)ethyl]phthalimide, ethyl acetate solvate (37.6 g., 0.0675 mole) and absolute ethanol (340 ml.) is treated with hydrazine hydrate (7.43 g.) and warmed, under nitrogen, in an oil bath to 75° during 65 minutes, the bath is kept at this temperature for an additional 55 minutes. The mixture is then cooled in an ice bath, and the solid is collected by filtration and washed with absolute ethanol and methylene chloride. The combined filtrate is mixed with ice cold salt water and extracted with methylene chloride. The extract is washed with water, dried over anhydrous sodium sulfate and concentrated in vacuo. The residue is chromatographed on silica gel (1 kg.) with methanol and the resulting product is crystallized from methylene chloride to give ether 5.29 g., of melting point 198°–200°°C. dec. and 2.37 g., of melting point 194°–196.5° C. d. of 1-(2-aminoethyl)-8-chloro-6-phenyl-4H-s-triazolo[4,3-a][1,4]benzodiazepine. The analytical sample is crystallized from methanol-ethyl acetate and had a melting point of 205°–207°.

EXAMPLE 22

1-[2-Dimethylamino)ethyl]-8-chloro-6-phenyl-4H-s-triazolo[4,3-a][1,4]benzodiazepine bis cyclohexanesulfamate A stirred mixture of 1-(2-aminoethyl)-8-chloro-6-phenyl-4H-s-triazolo[4,3-a][1,4]benzodiazepine (1.69 g., 0.005 mole) and acetonitrile (30 ml.) is treated successively with 37% aqueous formaldehyde (2 ml.) and acetic acid (0.29 ml.) and cooled in an ice bath. To this mixture is added sodium cyanoborohydride (500 mg., 0.008 mole) and the resulting mixture is kept under nitrogen, in the ice bath for 35 minutes and at ambient temperature for 2 hours 10 minutes. Acetic acid (4 drops) is added during the latter period to maintain a pH of about 7. The mixture is poured into cold water; the solution is saturated with sodium chloride and extracted with chloroform. The extract is washed with brine, dried over anhydrous sodium sulfate and concentrated. The residue is chromatographed on silica gel (100 g.) with methanol to give 1.20 g. of 1-[2-dimethylamino)ethyl]-8-chloro-6-phenyl-4H-s-triazolo[4,3-a]-[1,4]benzodiazepine as an oil. A solution of this oil in ethyl acetate is treated with an equal weight (1.2 g.) of cyclohexane-sulfamic acid in methanol and the resulting salt is crystallized to give 2.16 g. of 1-[2-(dimethylamino)-ethyl]-8-chloro-6-phenyl-4H-s-triazolo[4,3-a][1,4]benzodiazepine bis cyclohexanesulfamate. The analytical sample is prepared by recrystallizing some of this material from ethanol-ethyl acetate and has a melting point of 132°–139° C.

Anal. calcd. for $C_{32}H_{46}ClN_7P_6S_2$: C, 53.06; H, 6.40; Cl, 4.89; N, 13.54; S, 8.85. Found: C, 52,73; H, 6.70; Cl, 4.61; N, 13.31; S, 8.84.

EXAMPLE 23

1-[2-(Dimethylamino)ethyl]-8-chloro-5,6-dihydro-6-phenyl-4H-s-triazolo[4,3-a][1,4]benzodiazepine A stirred mixture of 1-[2-(dimethylamino)ethyl]-8-chloro-6-phenyl-4H-s-triazolo[4,3-a][1,4]benzodiazepine (3.66 g., 0.01 mole) in tetrahydrofuran (100 ml.) is cooled in an ice bath, under nitrogen, and treated with 20 ml. of a 1M solution of borane in tetrahydrofuran. The mixture is allowed to warm to ambient temperature (22°–25°) and stand for 18 hours. It is then refluxed for 1 hour, cooled in an ice bath and treated with 3 ml. of 6N hydrochloric acid. This mixture is boiled for 3 hours with distillation. During this period methanol is added so that the volume of the mixture remains about constant. The mixture is then concentrated in vacuo. The residue is mixed with water, neutralized with sodium bicarbonate and extracted with chloroform. The extract is washed with brine, dried over anhydrous sodium sulfate and concentrated in vacuo. The residue is dissolved in methanol (70 ml.) mixed with 25% aqueous ethylene diamine (42 ml.) and refluxed for 3 hours. The mixture is concentrated to remove methanol, diluted with salt water and extracted with chloroform. The extract is washed with brine, dried over anhydrous sodium sulfate and concentrated in vacuo. The residue is chromatographed over silica gel (200 g.) with methanol. The product thus obtained is crystallized from ethyl acetate-Skellysolve B (hexanes) to give 1-[2-(dimethylamino)ethyl]-8-chloro-5,6-dihydro-6-phenyl-4H-s-triazolo[4,3-a][1,4]benzodiazepine of melting point 131°–137° C.

EXAMPLE 24

1-[2-(Diethylamino)ethyl]-8-chloro-6-phenyl-4H-s-triazolo[4,3-a][1,4]benzodiazepine In the manner given in Example 22, a mixture of 1-(2-aminoethyl)-8-chloro-6-phenyl-4H-s-triazolo[4,3-a][1,4]benzodiazepine, acetaldehyde and acetic acid in acetonitrile is treated with sodium cyanoborohydride and the resulting boron complex is warmed with aqueous ethylenediamine to give 1-[2-(diethylamino)ethyl]-8-chloro-6-phenyl-4H-s-triazolo-[4,3-a][1,4]benzodiazepine.

EXAMPLE 25

1-[2-(Dipropylaminoethyl]-8-chloro-6-phenyl-4 H-s-triazolo[4,3-a][1,4]benzodiazepine In the manner give in Example 22, a mixture of 1-(2-aminoethyl)-8-chloro-6-phenyl-4H-s-triazolo[4,3-a][1,4]-benzodiazepin, propionaldehyde and acetic acid in tetrahydrofuran is treated with sodium cyanoborohydride and the resulting boran complex is warmed with aqueous ethylenediamine to give 1-[2-(dipropylamino)ethyl]-8-chloro-6-phenyl-4H-s-triazolo[4,3-a][1,4]benzodiazepine.

EXAMPLE 26

N-[2-(8-chloro-6-phenyl-4H-s-triazolo[4,3-a]-[1,4]benzodiazepin-1-yl)propyl]phthalimide and its methanol solvate A stirred mixture of 3-phthalimidobutyric acid (C. Ainsworth and R. G. Jones, J. Amer. Chem. Soc. 76, 5651 (1954)), (12.82 g., 0.055 mole), and tetrahydrofuran (100 ml.) is cooled under nitrogen in an ice-bath and treated with carbonyldiimidazole (8.96 g., 0.055 mole). The mixture is allowed to warm to ambient temperature and stand for 1 hour 15 minutes. It is then cooled in an ice-bath and treated with 7-chloro-2-hydrazino-5-phenyl-3H-1,4-benzodiazepine (14.24 g., 0.05 mole) and tetrahydrofuran (1000 ml.). This mixture is stirred at ambient temperature (22°–25° C.) for 18 hours. The finely divided white solid which results is collected by filtration, washed with tetrahydrofuran and dried to give 25 g. of 3-phthalimidobutyric acid, 2-(7-chloro-5-3H-1,4-benzodiazepin-2-yl)hydrazide. This is mixed, with stirring, during 5 minutes with acetic acid (250 ml.) which had been warmed to 97° C. for 30 minutes, cooled and concentrated in vacuo. The residue is mixed with chloroform and water, neutralized with sodium bicarbonate and extracted with chloroform. The extract is washed with brine, dried over anhydrous sodium sulfate and concentrated. The residue is dissolved in methanol, decolorized with activated charcoal and crystallized from methanol-ethyl acetate to give: 17.17 g. of N-[2-(8-chloro-6-phenyl-4H-s-triazolo[4,3-a][1,4]benzodiazepin-1-yl)propyl]phthalimide as its methanol solvate of melting point 237.5°–241° C. and a second crop of 0.99 g., of melting point 237°–237.5° C. The analytical sample has a melting point of 237.5°–239° C.

Anal. calcd. for $C_{27}H_{20}ClN_5O_2 \cdot 1/2CH_3OH$: C, 66.33; H, 4.45; Cl, 7.12; N, 14.06; MeOH, 3.22. Found: C, 66.88; H, 4.59; Cl, 7.17; N, 13.80; MeOH, 3.13.

Crystallizing this product from absolute ethanol gives the pure unsolvated product of melting point 238°–240.5° C.

EXAMPLE 27

1-(2-aminopropyl)-8-chloro-6-phenyl-4H-s-triazolo[4,3-a][1,4]benzodiazepine bistosylate hydrate A stirred suspension of N-[2-(8-chloro-6-phenyl-4H-s-triazolo[4,3-a][1,4]benzodiazepin-1-yl)propyl]phthalimide (4.82 g., 0.01 mole) and absolute ethanol (50 ml.) is treated with hydrazine hydrate (0.75 g., 0.015 mole) and warmed in a oil bath to 77° C. during 2 hours 20 minutes. During this time the starting material dissolves and a second solid begins to form. The mixture is kept at about 77° C. for 1 hour, cooled in an ice bath and filtered. The solid is washed with ethanol and methylene chloride and the combined filtrate concentrated in vacuo. The residue is mixed with water and extracted with $CHCl_3$; the extract is washed with brine, dried over anhydrous sodium sulfate and concentrated in vacuo. The residue was chromatographed on silica gel (250 g.) with methanol to give 1-(2-aminopropyl)-8-chloro-6-phenyl-4H-s-triazolo[4,3][1,4-]benzodiazepine as an oil. This product is dissolved in ethyl acetate and treated with a solution of two equivalents of p-toluenesulfonic acid in methanol. The resulting salt is recrystallized from methanol-ethyl acetate to give 1-(2-aminopropyl)-8-chloro-6-phenyl4H-s-triazolo[4,3-a][1,4]benzodiazepine bistosylate hydrate in three crops: 0.312 g. of melting point 288.5°–230° C.; 1.429 g. of melting point 225°–226.5° C. and 0.174 g. of melting point 227°–228.5° C. The analytical sample had a melting point of 230°–233° C.

Anal. calcd. for $C_{33}H_{36}ClN_5O_7S_2$: C, 55.49; H, 5.08; Cl, 4.96; N, 9.80; S, 8.99. Found: C, 55.94; 55.21; H, 5.04, 4.95; Cl, 5.16; N, 9.86; 9.42; S, 8.94.

EXAMPLE 28

N-[2-[8-chloro-6-(o-chlorophenyl)4H-s-triazolo[4,3-a][1,4]benzodiazepin-1-yl]propyl]phthalimide In the manner given in Example 26, 3-phthalimidobutyric acid and carbonyldiimidazol are reacted in tetrahydrofuran. To this mixture is added 7-chloro-2-hydrazino-(o-chlorophenyl)-3H-1,4-benzodiazepine to give 3-phthalimidobutyric acid, 2-[7-chloro-5-(o-chlorophenyl)3H-1,4-benzodiazepin-2-yl]hydrazide which is warmed with acetic acid to give N-[2-[8-chloro-6-(o-chlorophenyl)-4H-s-triazolo-[4,3-a][1,4]benzodiazepin-1-yl]propyl]phthalimide.

EXAMPLE 29

1-[2-aminopropyl]-8-chloro-6-(o-chlorophenyl)-4H-s-triazolo[4,3-a][1,4]benzodiazepine In the manner given in Example 27, a solution of N-[2-[8-chloro-6:(o-chlorophenyl)-4H-s-triazolo[4,3-a][1,4]-benzodiazepin-1-yl]propyl]phthalimide in ethanol is heated with hydrazine hydrate to give 1-(2-aminopropyl)-8-chloro-6-(o-chlorophenyl)-4H-s-triazolo[4,3-a][1,4]benzodiazepine.

EXAMPLE 30

1-[2-(methylamino)propyl]-8-chloro-6-(o-chlorophenyl)-4H-s-triazolo[4,3-a][1,4]benzodiazepine A solution of 0.001 mole of 1-(2-aminopropyl)-8-chloro-6-(o-chlorophenyl)-4H-s-triazolo[4,3-a][1,4]benzodiazepine in acetonitrile is successively treated with 0.001 mole each of formaldehyde, acetic acid and sodium cyanoborohydride at room temperature. The mixture is concentrated in vacuo and the residue treated with 25% aqueous ethylene diamine (5 ml.) and methanol (10 ml.) and refluxed under nitrogen for 2 hours. This mixture is concentrated and the residue mixed with water and extracted with chloroform. The chloroform extracts were filtered, evaporated, and crystallized to give 1-[2-(methylamino)-propyl]-8-chloro-6-(o-chlorophenyl)-4H-s-triazolo[4,3-a][1,4]benzodiazepin.

EXAMPLE 31

1-[2-[(dimethylamino)propyl]-8-chloro-6-(o-chlorophenyl)-4H-s-triazolo[4,3-a][1,4]benzodiazepine.

In the manner given in Example 22, 1-(2-aminopropyl)-8-chloro-6-(o-chlorophenyl)-4H-s-triazolo[4,3-a][1,4]benzodiazepine in acetonitrile is treated with 37% aqueous formaldehyde and acetic acid and thereafter with sodium cyanoborohydride to give 1-[2-[(dimethylamino)propyl]-8-chloro-6-(o-chlorophenyl]-4H-s-triazolo[4,3-a][1,4]benzodiazepine.

EXAMPLE 32

1-[2-(N-ethyl-N-methylamino)propyl]-8-chloro-6-(o-chlorophenyl)-4H-s-triazolo[4,3-a][1,4]benzodiazepine In the manner given in Example 22, 1-[2-(methylamino)-propyl]-8-chloro-6-(o-chlorophenyl)-4H-s-triazolo[4,3-a]-[1,4]benzodiazepine is treated successively with acetaldehyde and sodium cyanoborohydride to give 1-[2-N-ethyl-N-methylamino)propyl]-8-chloro-6-(o-chlorophenyl)-4H-s-triazolo[4,3-a][1,4]benzodiazepine.

EXAMPLE 33

N-[2-[8-nitro-6-(o-chlorophenyl)-4H-s-triazolo-[4,3-a][1,4]benzodiazepin-1-yl]butyl]phthalimide In the manner given in Example 20, 3-phthalimidovaleric acid and carbonyldiimidazol are reacted in tetrahydrofuran. To this mixture is added 7-nitro-2-hydrazino-5-(o-chlorophenyl)-3H-1,4-benzodiazepine to give 3-phthalimidovaleric acid, 2-(7-nitro-5-(o-chlorophenyl)-3H-1,4-benzodiazepin-2-yl)hydrazide which is warmed with acetic acid to give N-[2-[8-nitro-6-(o-chlorophenyl)-4H-s-triazolo[4,3-a][1,4]benzodiazepin-1-yl]butyl]phthalimide.

EXAMLE 34

1-(2-aminobutyl)-8-nitro-6-(o-chlorophenyl)-4H-s-triazolo[4,3-a][1,4]benzodiazepine In the manner given in Example 21, a solution of N-[2-[8-nitro-6-(o-chlorophenyl)-4H-s-triazolo[4,3-a][1,4]-benzodiazepin-1-yl]butyl]phthalimide in ethanol is heated with hydrazine hydrate to give 1-(2-aminobutyl)-8-nitro-6-(o-chlorophenyl)-4H-s-triazolo[3,4-a][1,4]benzodiazepine.

EXAMPLE 35

1-[2-[(diethylamino)butyl]-8-nitro-6-(o-chloro)-phenyl]-4H-triazolo[4,3-a][1,4]benzodiazepine In the manner given in Example 22, 1-(2-aminobutyl)-8-nitro-6-(o-chlorophenyl)-4H-s-triazolo[3,4-a][1,4]benzodiazepine in acetonitrile is treated with acetaldehyde and acetic acid and thereafter with sodium cyanoborohydride and the resulting boron complex was warmed with aqueous ethylene diamine to give 1-[2-[(diethylamino)butyl]-8-nitro-6-(o-chlorophenyl)-4H-s-triazolo[4,3-a][1,4]benzodiazepine.

EXAMPLE 36

N-[2-[8-chloro-6-fluorophenyl)-4H-s-triazolo[4,3-a][1,4]benzodiazepin-1-yl]propyl]phthalimide In the manner given in Example 20, 3-phthalimidobutyric acid and carbonyldiimidazol are reacted in tetrahydrofuran. To this mixture is added 8-chloro-2-hydrazino-5-(2,6-difluorophenyl)-3H-1,4-benzodiazepine to give 3-phthalimidobutyric acid, 2-[7-chloro-6-(2,6-difluorophenyl)-3H-1,4-benzodiazepin-2-yl]hydrazide which is warmed with acetic acid to give N-[2-[8-chloro-6-(2,6-difluorophenyl)-4H-s-triazolo[4,3-a][1,4]benzodiazepin-1-yl]propyl]phthalimide.

EXAMPLE 37

1-(2-aminopropyl)-8-chloro-6-(2,6-difluorophenyl)-4H-s-triazolo[4,3-a][1,4]benzodiazepine In the manner given in Example 21, a solution of N-[2-[8-chloro-6-(2,6-difluorophenyl)-4H-s-triazolo[4,3-a]-[1,4]benzodiazepin-1-yl]propyl]phthalimide in ethanol is heated with hydrazine hydrate to give 1-(2-aminopropyl)-8-chloro-6-(2,6-difluorophenyl)-4H-s-triazolo[4,3-a][1,4]-benzodiazepine.

EXAMPLE 38

N-[2-8-chloro-6-(o-chlorophenyl)-4H-s-triazolo[4,3-a][1,4]benzodiazepin-1-yl)ethyl]phthalimide In the manner given in Example 20, 3-phthalimidopropionic acid and carbonyldiimidazol are reacted in tetrahydrofuran. To this mixture is added 2-hydrazino-5-(o-chlorophenyl)-3H-1,4-benzodiazepine to give 3-phthalimidopropionic acid, 2-[7-chloro-6-(o-chlorophenyl)-3H-1,4-benzodiazepin-2-yl]hydrazide which is warmed with acetic acid to give n-[2-[8-chloro-6-(o-chlorophenyl)-4H-s-triazolo[4,3-a][1,4]benzodiazepin-1-yl]ethyl]phthalimide.

EXAMPLE 39

1-(2-aminoethyl)-8-chloro-6-(o-chlorophenyl)-4H-s-triazolo[4,3-a][1,4]benzodiazepine In the manner given in Example 21, a mixture of N-[2-[8-chloro-6-(o-chlorophenyl)-4H-s-triazolo[4,3-a][1,4]benzodiazepin-1-yl]ethyl]phthalimide is heated with hydrazine hydrate to give 1-(2-aminoethyl)-8-chloro-6-(o-chlorophenyl)-4H-s-triazolo[4,3-a][1,4]benzodiazepin.

EXAMPLE 40

1-[2-(Dimethylamino)ethyl]-8-chloro-6-(o-chlorophenyl)-4H-s-triazolo[4,3-a][1,4]benzodiazepine In the manner given in Example 22, a mixture of 1-(2-aminoethyl)-8-chloro-6-(o-chlorophenyl)-4H-s-triazolo[4,3-a][1,4]benzodiazepine, 37% aqueous formaldehyde and acetic acid in acetonitrile is treated with sodium cyanoborohydride and the resulting boron complex is warmed with aqueous ethylenedizmine to give 1-[2-(dimethylamino)ethyl]-8-chloro-6-(o-chlorophenyl)-4H-s-triazolo[4,3-a][1,4]benzodiazepine

EXAMPLE 41

1-[2-[(dipropylamino)ethyl]-8-chloro-6-(o-chlorophenyl)-4H-s-triazolo[4,3-a][1,4]benzodiazepine In the manner given in Example 22, a mixture of 1-(2-aminoethyl)-3-chloro-6-(o-chlorophenyl)-4H-s-triazolo-[4,3-a][1,4]benzodiazepine in acetonitrile is treated with propionic acid aldehyde and acetic acid and thereafter with sodium cyanoborohydride and the resulting boron complex is warmed with aqueous ethylenediamine to give 1-[2-[(dipropylamino)ethyl]-8-chloro-6-(o-chlorophenyl)-4H-s-triazolo[4,3-a][1,4]benzodiazepine.

EXAMPLE 42

N-[2-[8-chloro-6-(o-fluorophenyl)-4H-s-triazolo[4,3-a][1,4]benzodiazepin-1-yl]propyl]phthalimide In the manner given in Example 20, 3-phthalimidobutyric acid and carbonyldiimidazol are reacted in tetrahydrofuran. To this mixture is added 7-chloro-2-hydrazino-5-(o-fluorophenyl)-3H-1,4-benzodiazepine to give 3-phthalimidobutyric acid 2-[7-chloro-5-(o-fluorophenyl)-3H-1,4-benzodiazepin-2yl]-hydrazide which is warmed with acetic acid to give N-[2-[8-chloro-6-(o-fluorophenyl)-4H-s-triazolo-[4,3-a][1,4]benzodiazepin-1-yl]propyl]phthalimide

EXAMPLE 43

1-(2-aminopropyl)-8-chloro-6-(o-fluorophenyl)-4H-s-triazolo[4,3-a][1,4]benzodiazepine In the manner given in Example 21, a solution of N-[2-[8-chloro-6-(o-fluorophenyl)-4H-s-triazolo[4,3-a][1,4]-benzodiazepin-1-yl]propyl]phthalimide in ethanol is heated with hydrazine hydrate to give 1-(2-aminopropyl)-8-chloro-6-(o-fluorophenyl)-4H-s-triazolo[4,3-a][1,4]benzodiazepine.

EXAMPLE 44

1-[2-[(dimethylamino)propyl]-8-chloro-6-(o-fluorophenyl)-4H-s-triazolo[4,3-a][1,4]benzodiazepine In the manner given in Example 22, 1-(2-aminopropyl)-8-chloro-6-(o-fluorophenyl)-4H-s-triazolo[4,3-a][1,4]benzodiazepine in acetonitrile is treated with 37% aqueous formaldehyde and acetic acid and thereafter with sodium cyanoborohydride and the resulting boron complex is warmed with aqueous ethylene diamine to give 1-[2-[(dimethylamino)-propyl]-8-chloro-6-(o-fluorophenyl)-4H-s-triazolo[4,3-a][1,4]benzodiazepine.

EXAMPLE 45

N-[2-(8-chloro-6-phenyl-4H-s-triazolo[4,3-a]-[1,4]benzodiazepin-1-yl)butyl]phthalimide In the manner given in Example 20, 3-phthalimidovaleric acid and carbonyldiimidazole are allowed to react in tetrahydrofuran. To this mixture is added 7-chloro-2-hydrazino-5-phenyl-3H-1,4-benzodiazepine to give 3-phthalimidovaleric acid, 2-(7-chloro-5-phenyl-3H-1,4-benzodiazepin-2-yl)hydrazide which is warmed with acetic acid to give N-[2-(8-chloro-6-phenyl-4H-s-triazolo[4,3-a][1,4]benzodiazepin-1-yl)butyl]phthalimide

EXAMPLE 46

1-(2-Aminobutyl)-8-chloro-6-phenyl-4H-s-triazolo[4,3-a][1,4]benzodiazepine

In the manner given in Example 21, N-[2-(8-chloro-6-phenyl-4H-s-triazolo[4,3-a][1,4]benzodiazepin-1-yl)butyl]-phthalimide in ethanol is warmed with hydrazine hydrate to give 1-(2-aminobutyl)-8-chloro-6-phenyl-4H-s-triazolo[4,3-a]-[1,4]benzodiazepine.

EXAMPLE 47

1-(2-aminopropyl)-8-chloro-5,6-dihydro-6-phenyl-4H-s-triazolo[4,3-a][1,4]benzodiazepine In the manner given in Example 23 a mixture of 1-(2-aminopropyl)-8-chloro-6-phenyl-4H-s-triazolo[4,3-a][1,4]-benzodiazepine and tetrahydrofuran was treated with borane to give 1-(2-aminopropyl)-8-chloro-5,6-dihydro-6-phenyl-4H-s-triazolo[4,3-a][1,4]benzodiazepine.

In the manner given in the preceding examples, other compounds of formula X can be produced such as:
1-[2-(dimethylamino)ethyl]-6-(o-nitrophenyl)-8-trifluoromethyl-4H-s-triazolo[4,3-a][1,4]benzodiazepine;

1-(2-aminoethyl)-6-(m-bromophenyl)-7-ethoxy-4H-s-triazolo-[4,3-a][1,4]benzodiazepine;

1-[2-(dimethylaminoethyl)-6-(p-fluorophenyl)-8-(ethylthio)-4H-s-triazolo[4,3-a][1,4]benzodiazepine;

1-[2-(diethylamino)propyl]-6-(2,4-dimethoxyphenyl)-9-bromo-4H-s-triazolo[4,3-a][1,4]benzodiazepine;

1-(2-pyrrolidinoethyl)-6-(m-nitrophenyl)-10-ethoxy-4H-s-triazolo[4,3-a][1,4]benzodiazepine 1-(2-piperidinoethyl)-6-(p-isopropoxyphenyl)-7-fluoro-4H-s-triazolo[4,3-a][1,4]benzodiazepine;

1-(2-morpholinoethyl)-6-(o-chlorophenyl)-8,10-dichloro-4H-s-triazolo[4,3-a][1,4]benzodiazepine;

1-[2-(4-methylpiperazino)ethyl]-6-(o-fluorophenyl)-7-methylthio)-4H-s-triazolo[4,3-a][1,4]benzodiazepine; 1-(2-aminoethyl)-8-nitro-6-(o-chlorophenyl)-4H-s-triazolo-[4,3-a][1,4]benzodiazepine;

1-(2-aminopropyl)-6-(4,6-dimethyloxyphenyl)-7-fluoro-4H-s-triazolo[4,3-a][1,4]benzodiazepine;

1-[2-(dimethylamino)propyl]-8-(propylthio)-7-chloro-6-(o-chlorophenyl)-4H-s-triazolo[4,3-a][1,4]benzodiazepine;

1-[2-(diethylamino)butyl]-8,10-difluoro-6-phenyl-4H-s-triazolo[4,3-a][1,4]benzodiazepine;

1-[2-(N-methyl-N-propylamino)ethyl]-5,6-dihydro-6-(o-nitrophenyl)-8-trifluoromethyl-4H-s-triazolo[4,3-a][1,4]benzodiazepine;

1-[2-(methylamino)ethyl]-5,6-dihydro-6-(m-bromophenyl)-7-ethoxy-4H-s-triazolo[4,3-a][1,4]benzodiazepine;

1-[2-(dimethylamino)ethyl]-5,6-dihydro-6-(p-fluorophenyl)-8-ethylthio)-4H-s-triazolo[4,3-a][1,4]benzodiazepine;

1-[2-(diethylamino)propyl]-5,6-dihydro-6-(2,4-dimethoxyphenyl)-9-bromo-4H-s-triazolo[4,3-a][1,4]benzodiazepine;

1-(2-pyrrolidinoethyl)-5,6-dihydro-6-(m-nitrophenyl)-10-ethoxy-4H-s-triazolo[4,3-a][1,4]benzodiazepine;

1-(2-piperidinoethyl)-5,6-dihydro-6-(p-isopropoxyphenyl)-7-fluoro-4H-s-triazolo[4,3-a][1,4]benzodiazepine;

1-(2-morpholinoethyl)-5,6-dihydro-6-(o-chlorophenyl)-8,10-dichloro-4H-s-triazolo[4,3-a][1,4]benzodiazepine;

1-[2-(4-methylpiperazino)ethyl]-5,6-dihydro-6-(o-fluorophenyl)-7-(methylthio)-4H-s-triazolo[4,3-a][1,4]benzodiazepine;

1-(2-aminoethyl)-8-nitro-5,6-dihydro-(o-chlorophenyl)-4H-s-triazolo[4,3-a][1,4]benzodiazepine;

1-(2-aminopropyl)-5,6-dihydro-6-(4,6-dimethoxyphenyl)-7-fluoro-4H-s-triazolo[4,3-a][1,4]benzodiazepine;

1-[2-(dimethylamino)propyl]-8-(propylthio)-7-chloro-5,6-dihydro-6-(o-chlorophenyl)-4H-s-triazolo[4,3-a][1,4]benzodiazepine; 1-[3-(diethylamino)butyl]-8,10-difluoro-5,6-dihydro-6-phenyl-4H-s-triazolo[4,3-a][1,4]benzodiazepine; and the like.

The pharmacologically acceptable acid addition salts of compounds of formula X (as well as of formula XI and XII) can be prepared and isolated by conventional processes, such as reacting a compound of formula X with a selected pharmacologically acceptable acid. Such acids include hydrochloric, hydrobromic, phosphoric, sulfuric, acetic, tartaric, lactic, citric, malic, maleic, methanesulfonic, benzenesulfonic, cyclohexanesulfonic acids, toluenesulfonic, and the like. The reaction is conveniently performed in an organic solvent e.g. ether, dioxane or tetranydrofuran, ethanol, methanol, ethyl acetate; the salts can be recovered by crystallization, precipitation or evaporating the solvent.

I claim:

1. A 1-(2-aminoalkyl)-6-phenyltriazolobenzodiazepine compound of the formula:

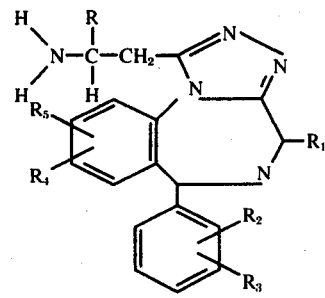

wherein R is hydrogen, methyl, or ethyl; wherein $R_1$ is hydrogen or methyl; wherein $R_2$, $R_3$, $R_4$ and $R_5$ are selected from the group consisting of hydrogen, alkyl of 1 to 3 carbon atoms, halogen, nitro, trifluoromethyl, and alkoxy, and alkylthio, in which the carbon chain moiety is of 1 to 3 carbon atoms, inclusive, and the pharmacologically acceptable acid addition salts thereof.

2. 1-[2-(dimethylamino)ethyl]-8-chloro-6-phenyl-4H-s-triazolo-[4,3-a][1,4]benzodiazepine.

3. A compound according to claim 2 as the biscyclohexanesulfamic acid salt.

4. 1-[2-(dimethylamino)ethyl-8-chloro-5,6-dihydro-6-phenyl-4H-s-triazolo[4,3-a][1,4]benzodiazepine.

* * * * *

UNITED STATES PATENT OFFICE
CERTIFICATE OF CORRECTION

Patent No. 4,012,413　　　　　　　　　　Dated　March 15, 1977

Inventor(s)　Jackson B. Hester, Jr.

It is certified that error appears in the above-identified patent and that said Letters Patent are hereby corrected as shown below:

| | |
|---|---|
| Title Page at [63]: | "138,827" should read -- 138,287 -- |
| Column 1, line 10: | "3,789,943" should read -- 3,759,943 -- |
| Column 7, lines 49-50: | "6 x 11 x 5" should read -- 6"x11"x5" -- |
| line 56: | "2-di..." should read -- 2-(di... -- |
| line 59: | "phenyl4H" should read -- phenyl-4H -- |
| Column 8, line 33: | "carries" should read -- carriers -- |
| Column 10, line 57: | "3a" should read -- 3-a -- |
| Column 11, line 22: | "202°-203°" should read -- 202-203° -- |
| line 32: | "]-[" should read -- ][ -- |
| Column 12, line 14: | "tiazolo" should read -- triazolo -- |
| Column 13, line 3: | "...aino)" should read -- ...amino) -- |
| line 26: | "m/." should read -- ml. -- |
| line 54: | "[1,4benzo..." should read -- [1,4]benzo... -- |
| Column 14, line 20: | "]-[" should read -- ][ -- |
| line 32: | "]-[" should read -- ][ -- |
| line 35: | "[1,4ben..." should read -- [1,4]ben... -- |
| line 41: | "]-ben..." should read -- ]ben... -- |
| line 47: | "]-ben..." should read -- ]ben... -- |
| line 68: | "a]-[1," should read -- a][1, -- |
| Column 15, line 21: | "]-[" should read -- ][ -- |
| line 31: | ")-ethyl" should read -- )ethyl -- |
| line 32: | "]-[" should read -- ][ -- |
| line 53: | ")-ethyl" should read -- )ethyl -- |
| line 54: | "]-[" should read -- ][ -- |
| line 62: | "5,6 dihydro" should read -- 5,6-dihydro -- |
| Column 16, line 42: | "[1,4-ben..." should read -- [1,4]ben... -- |
| line 45: | "tiazolo" should read -- triazolo -- |
| line 62: | "1 yl" should read -- 1-yl -- |
| Column 17, line 24: | "130-133.5°" should read -- 130.5-133.5° -- |
| Column 18, line 11: | "]-[" should read -- ][ -- |
| line 15: | ")-ethyl]" should read -- )ethyl] -- |
| Column 19, line 7: | "[1,4]-ben..." should read -- [1,4]ben... -- |
| line 16: | "a]-" should read -- a][ -- |

UNITED STATES PATENT OFFICE
CERTIFICATE OF CORRECTION

Patent No. 4,012,413            Dated    March 15, 1977

Inventor(s)   Jackson B. Hester, Jr.

It is certified that error appears in the above-identified patent and that said Letters Patent are hereby corrected as shown below:

```
Column 19, line 28:     "(1000 ml)" should read (100 ml) --
Column 20, line 3:      "CHCll₃" should read -- CHCl₃ --
           line 13:     "phenyl 4H-" should read -- phenyl-4H --
           line 25:     ")4H" should read -- )-4H --
           line 33:     ")3H" should read -- )-3H --
           line 43:     "-6:(" should read -- -6-( --
Column 21, line 21:     ")-propyl" should read -- )propyl --
           line 22:     "]-[" should read -- ][ --
           line 50:     "]-benzo..." should read -- ]benzo... --
           line 54:     "[3,4-a" should read -- [4,3-a --
           lines 56-57: "chloro)-phenyl" should read -- chlorophenyl) --
Column 22, line 2:      "6-fluorophenyl)-" should read -- 6-(2,6-
                            fluorophenyl) --
           line 23:     "4,3-a]-[" should read -- [4,3-a][ --
           line 30:     "2-8-" should read -- 2-[8- --
           line 40:     "n-[2-" should read -- N-[2- --
```

Signed and Sealed this

Twenty-sixth Day of June 1979

[SEAL]

Attest:

RUTH C. MASON
*Attesting Officer*

DONALD W. BANNER
*Commissioner of Patents and Trademarks*

UNITED STATES PATENT AND TRADEMARK OFFICE
CERTIFICATE OF CORRECTION

PATENT NO.  : 4,012,413
DATED       : March 15, 1977
INVENTOR(S) : Jackson B. Hester, Jr.

It is certified that error appears in the above-identified patent and that said Letters Patent are hereby corrected as shown below:

Column 17, line 1 "mole). The" should read -- mole). The mixture is treated with an appropriate hydrazino compound of the formula V according to scheme B. The --.

Column 26, claim 1, lines 4-14, the number 5 nitrogen in the formula should read as follows:

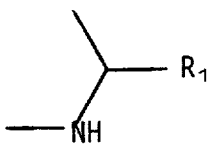

Signed and Sealed this

Fifteenth Day of April 1980

[SEAL]

Attest:

Attesting Officer

SIDNEY A. DIAMOND

Commissioner of Patents and Trademarks